United States Patent
Folch et al.

(10) Patent No.: US 9,518,977 B2
(45) Date of Patent: Dec. 13, 2016

(54) MICROFLUIDIC ASSAY APPARATUS AND METHODS OF USE

(71) Applicant: University of Washington through its Center for Commercialization, Seattle, WA (US)

(72) Inventors: Albert Folch, Seattle, WA (US); Raymond J. Monnat, Seattle, WA (US); Chi-ting Chang, Seattle, WA (US); Lisa Horowitz, Seattle, WA (US); Christopher G. Sip, Westlake Village, CA (US); Robert C. Rostomily, Seattle, WA (US)

(73) Assignee: University of Washington Through Its Center For Commercialization, Seattle, WA (US)

( * ) Notice: Subject to any disclaimer, the term of this patent is extended or adjusted under 35 U.S.C. 154(b) by 523 days.

(21) Appl. No.: 14/058,225

(22) Filed: Oct. 19, 2013

(65) Prior Publication Data
US 2014/0113838 A1    Apr. 24, 2014

Related U.S. Application Data

(60) Provisional application No. 61/770,063, filed on Feb. 27, 2013, provisional application No. 61/716,214, filed on Oct. 19, 2012.

(51) Int. Cl.
*G01N 33/50* (2006.01)
*G01N 33/53* (2006.01)
(Continued)

(52) U.S. Cl.
CPC ..... *G01N 33/5008* (2013.01); *B01L 3/502715* (2013.01); *C12M 23/12* (2013.01);
(Continued)

(58) Field of Classification Search
CPC ............ G01N 27/44791; G01N 33/5008; B01L 3/502715
(Continued)

(56) References Cited

U.S. PATENT DOCUMENTS 4,834,946 A * 5/1989 Levin .................. 435/287.2
5,942,443 A * 8/1999 Parce et al. ............ 506/39
(Continued)

FOREIGN PATENT DOCUMENTS

EP    1403518    8/2005
EP    1298198    10/2006
(Continued)

OTHER PUBLICATIONS

Orimo, et al., "Stromal fibroblasts in cancer—A novel tumor-promoting cell type," Cell cycle, 2006, 5,1597-1601.
(Continued)

*Primary Examiner* — Brian J Sines
(74) *Attorney, Agent, or Firm* — McDonnell Boehnen Hulbert & Berghoff LLP

(57) ABSTRACT

Methods and microfluidic apparatus are disclosed for drug prediction. A microfluidic apparatus has (a) a plate, (b) a plurality of wells defined in the plate, (c) a plurality of closed microchannels defined in the plate, and (d) a sample platform defining a plurality of open microchannels, where the plurality of closed microchannels are each in communication with one of the plurality of wells and one of the plurality of open microchannels of the sample platform.

18 Claims, 12 Drawing Sheets

(51) Int. Cl.
*B01L 3/00* (2006.01)
*C12M 1/32* (2006.01)
*C12M 3/06* (2006.01)

(52) U.S. Cl.
CPC ......... *C12M 23/16* (2013.01); *G01N 33/5304* (2013.01); *B01L 2200/027* (2013.01); *B01L 2300/0816* (2013.01); *B01L 2300/0829* (2013.01); *B01L 2300/0867* (2013.01); *B01L 2300/0877* (2013.01); *B01L 2300/10* (2013.01); *B01L 2400/0487* (2013.01)

(58) Field of Classification Search
USPC ....... 422/68.1, 502, 503, 551, 552, 553, 554
See application file for complete search history.

(56) References Cited

U.S. PATENT DOCUMENTS

| | | | | |
|---|---|---|---|---|
| 5,972,187 | A | * | 10/1999 | Parce et al. .................. 204/453 |
| 6,586,257 | B1 | * | 7/2003 | Vuong ........................... 436/165 |
| 7,312,085 | B2 | | 12/2007 | Chou |
| 7,378,280 | B2 | | 5/2008 | Quake |
| 7,504,069 | B2 | | 3/2009 | Williams |
| 7,749,444 | B2 | | 7/2010 | Yamada et al. |
| 2001/0049148 | A1 | * | 12/2001 | Wolk et al. ................... 436/180 |
| 2003/0041652 | A1 | * | 3/2003 | Spaid et al. .................. 73/54.05 |
| 2003/0044853 | A1 | | 3/2003 | Socks |
| 2003/0044992 | A1 | | 3/2003 | Chao |
| 2003/0157586 | A1 | | 8/2003 | Bonde |
| 2003/0215941 | A1 | | 11/2003 | Campbell et al. |
| 2005/0032072 | A1 | * | 2/2005 | Kautzer et al. .................... 435/6 |
| 2005/0175505 | A1 | | 8/2005 | Cantor et al. |
| 2005/0266582 | A1 | | 12/2005 | Modlin et al. |
| 2007/0122896 | A1 | | 5/2007 | Shuler |
| 2007/0154895 | A1 | * | 7/2007 | Spaid et al. ....................... 435/6 |
| 2012/0224053 | A1 | | 9/2012 | Vykoukal et al. |

FOREIGN PATENT DOCUMENTS

| | | |
|---|---|---|
| WO | 2005/033263 | 4/2005 |
| WO | 2012/050981 | 4/2012 |

OTHER PUBLICATIONS

Vaira, et al. "Preclinical model of organotypic culture for pharmacodynamic profiling of human tumors," Proceedings of the National Academy of Sciences of the United States of America, 2010, 107, 8352-8356.

Hattersley, et al., "Development of a microfluidic device for the maintenance and interrogation of viable tissue biopsies," Lab on a Chip, 2008, 8, 1842-1846.

Sunkara, et al., "Simple room temperature bonding of thermoplastics and poly(dimethylsiloxane)," Lab on a Chip, 2011, 11, 962-965.

de Graaf, "Preparation and incubation of precision-cut liver and intestinal slices for application in drug metabolism and toxicity studies," Nature protocols, 2010, 5, 1540-1551.

* cited by examiner

MICROFLUIDIC ASSAY APPARATUS AND METHODS OF USE

CROSS-REFERENCE TO RELATED APPLICATIONS

This application claims the benefit of the filing date of U.S. Provisional Patent Application Ser. No. 61/716,214, filed Oct. 19, 2012 and U.S. Provisional Patent Application Ser. No. 61/770,063, filed Feb. 27, 2013, which are hereby incorporated by reference in their entirety.

STATEMENT OF GOVERNMENT INTEREST

This invention was made with government support under grant numbers R01 EB001474 and PO1 CA077852 awarded by the National Institutes of Health. The government has certain rights in the invention.

BACKGROUND

Unless otherwise indicated herein, the materials described in this section are not prior art to the claims in this application and are not admitted to be prior art by inclusion in this section.

Drug prediction in cancer patients is often inaccurate. This is due to the heterogeneity of tumors and the difficulty associated with re-constructing a model for a given tumor. Therapy choice is often guided by population-based averages that do not reflect differences between tumors or between patients with a specific type of tumor. One approach to address this issue is DNA sequencing for personalized chemotherapy. DNA sequencing is utilized to capture key genetic mutations and to identify the drugs that specifically target these mutations. This genetic approach, however, does not account for the tumor microenvironment. In addition, tumor slice cultures have been used as a model for drug prediction. Tumor slices, however, may only be produced from large tumors and only after surgical extraction.

SUMMARY

Example embodiments provide a microfluidic apparatus and methods of use to establish a histopathologic diagnosis for drug prediction. For example, there are indications that tumor-stromal interactions play a key role in tumorigenesis and tumor progression and are responsible for drug responses in cancer patients. The present invention advantageously preserves the tissue architecture and maintains the tumor microenvironment, including tumor-stromal interactions, for drug prediction experiments. The apparatus and methods further beneficially act as a platform for needle core biopsy culture, the extraction of which is relatively less invasive than complete tumor removal. Needle core biopsies have the further advantage of being capable of rotation for additional experimentation, which multiplies the number of data points capable of being collected from a single tissue sample. The apparatus and methods may also be utilized with tumor slices. In addition, the apparatus and methods permit a large number of drugs or reagents to be tested on the sample tissue core or slice. The apparatus and methods are also user-friendly, permitting the drugs or reagents to be easily loaded into the device via pipette. The foregoing benefits and advantages of the microfluidic apparatus and methods of use help provide a more accurate prediction of drug responses and tumor chemosensitivity that can be applied directly to tumor biopsy material at the time of diagnosis. Thus, the apparatus and methods may help guide the choice of initial therapy in individual cancer patients.

Thus, in one aspect, a microfluidic apparatus is provided having (a) a plate, (b) a plurality of wells defined in the plate, (c) a plurality of closed microchannels defined in the plate, and (d) a sample platform defining a plurality of open microchannels, where the plurality of closed microchannels are each in communication with one of the plurality of wells and one of the plurality of open microchannels of the sample platform.

In another aspect, a method is provided including the steps of (a) providing a first plurality of reagents in a first set of a plurality of open microchannels in a sample platform, (b) providing a control media in a second set of the plurality of open microchannels in the sample platform, (c) providing a tissue sample disposed on a porous membrane, wherein the porous membrane is disposed on the sample platform, (d) providing, via an incubator, humid air in communication with the tissue sample and the porous membrane, and (e) perfusing the first plurality of reagents in the first set of the plurality of open microchannels and the control media in the second set of the plurality of open microchannels through the porous membrane and into the tissue sample via evaporative pumping.

These as well as other aspects, advantages, and alternatives, will become apparent to those of ordinary skill in the art by reading the following detailed description, with reference where appropriate to the accompanying drawings.

DETAILED DESCRIPTION

Example microfluidic apparatus and methods of use are described herein. Any example embodiment or feature described herein is not necessarily to be construed as preferred or advantageous over other embodiments or features. The example embodiments described herein are not meant to be limiting. It will be readily understood that certain aspects of the disclosed apparatus and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, "about" means+/−5%.

As used herein, "evaporative pumping" refers to the use of evaporation on a given surface to pump fluids through a medium towards that surface. The flow rate induced by evaporative pumping is a factor of humidity, temperature, air velocity, evaporation and diffusion. In practice, a tissue sample is maintained in humidified air and remains moist. Evaporation takes place at an air-fluid interface at the top surface of the tissue sample, aiding in nutrient transport through the tissue sample to maintain tissue viability. Evaporative pumping relies on the porous nature of the tissue sample, regardless of whether the tissue is alive or not.

As used herein, a "tissue sample" refers to a tissue core biopsy or a tissue slice. The tissue sample is preferably taken from a tumor, but may include healthy tissue as well.

As used herein, "perfusion" means to suffuse or permeate through tissue.

As used herein, a "reagent" means any therapeutic capable of perfusing through a tissue. In preferred embodiments, the therapeutics may be drugs that include chemotherapeutic agents or chemotherapy drugs, including combinations and titrations thereof. In additional preferred embodiments, the therapeutics may include biologics, such as T-cells, antibodies, etc., nanoparticles with therapeutic functionality or radiation, including conventional external beam or targeted delivery as conjugates with homing ligands, alone or in combination with "conventional" drugs.

As used herein, "control media" means plain cell culture medium capable of perfusing through a tissue. The control media is used to provide a control in between reagents perfusing the tissue sample and to maintain viability of the tissue sample.

Figure 1:
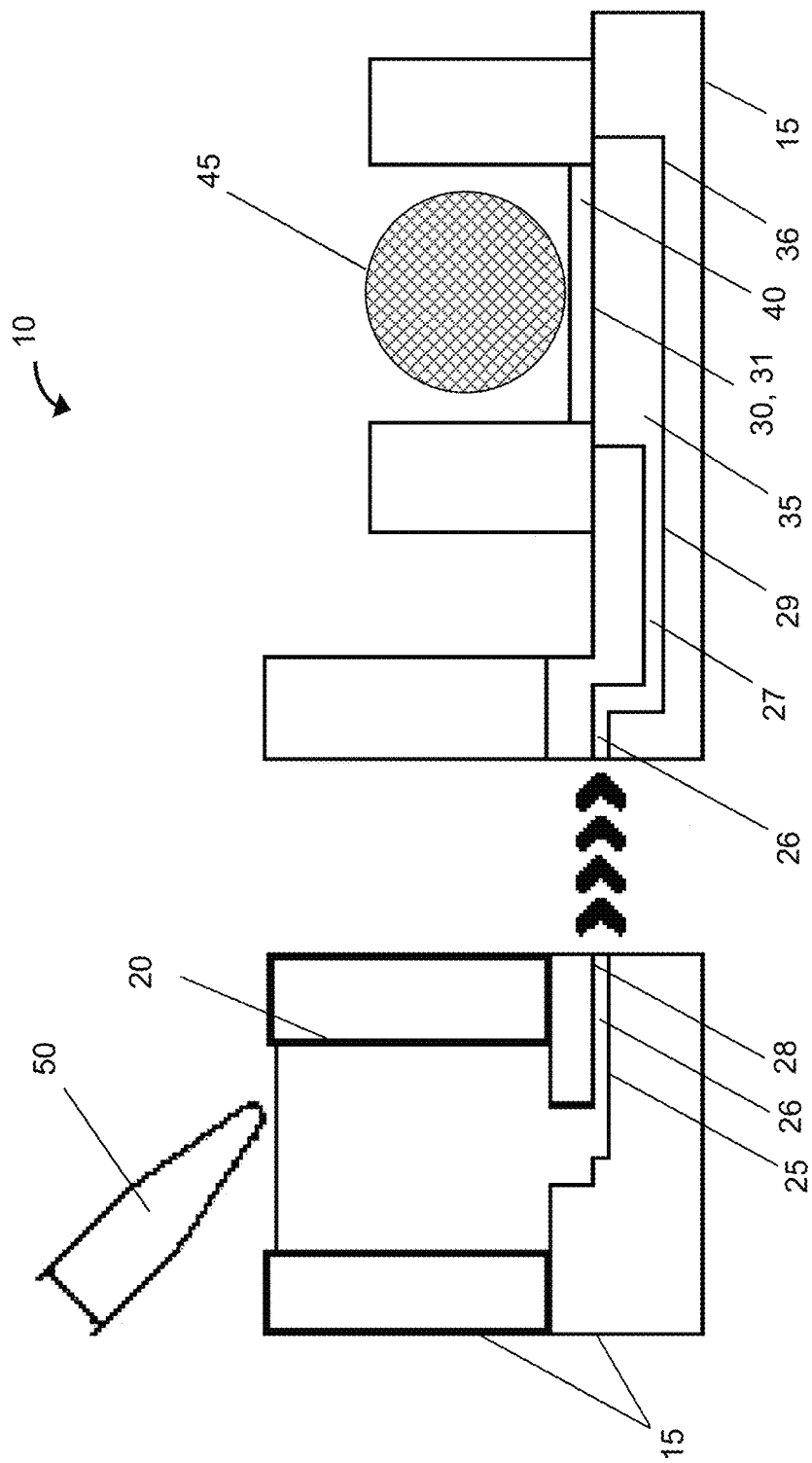
FIG. 1 is a partial cross-sectional side view of the microfluidic apparatus according to an example embodiment.
Figure 2:
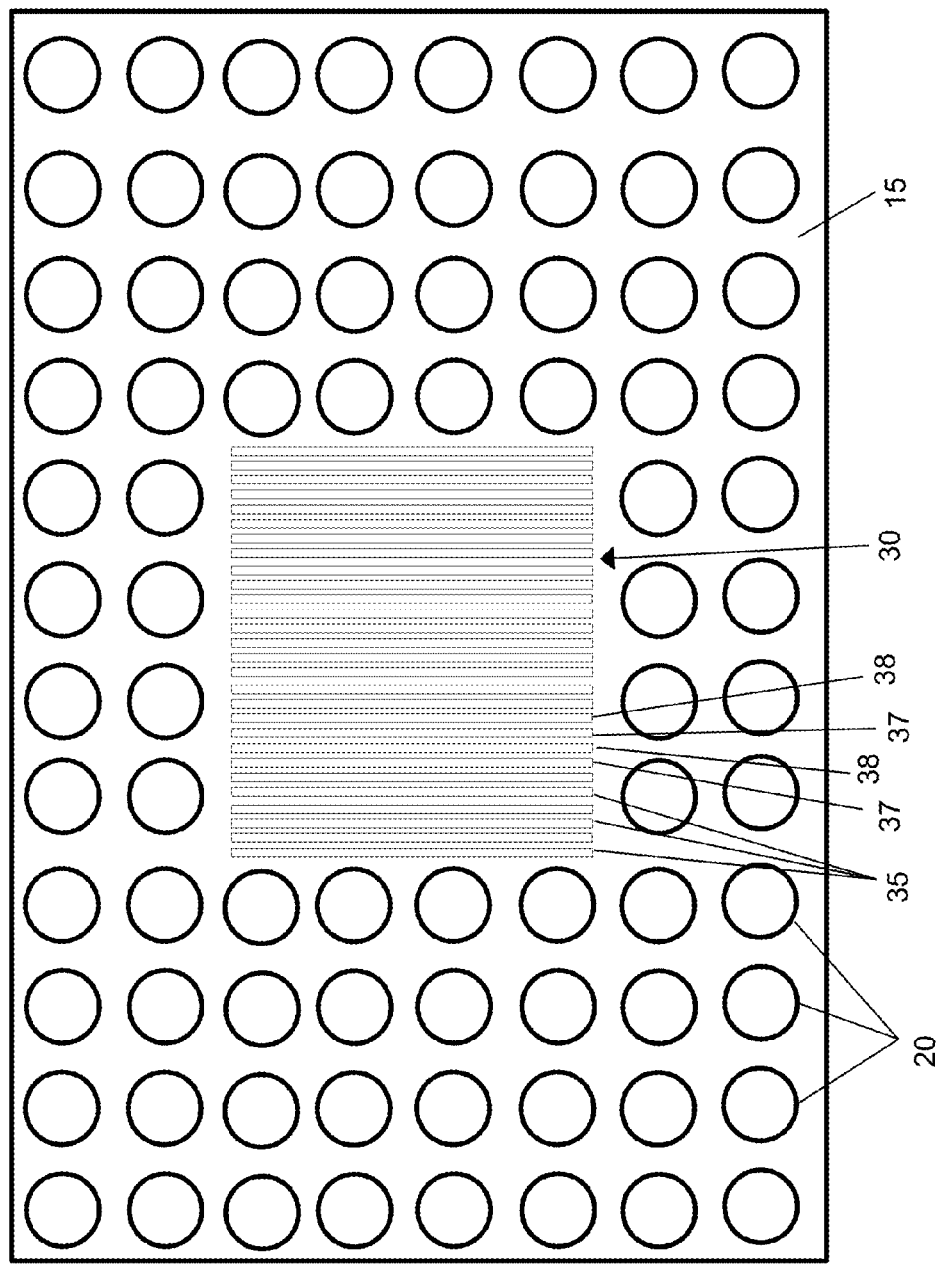
FIG. 2 is a top view of the microfluidic apparatus according to an example embodiment.

The present embodiments advantageously provide an apparatus and methods for drug prediction. Referring now to FIGS. 1-2, a microfluidic apparatus 10 is shown having a plate 15 and a plurality of wells 20 defined in the plate 15. In a preferred embodiment, the plurality of wells 20 each have the same volume. In various embodiments, the plurality of wells 20 comprises ten to one hundred wells.

The microfluidic apparatus 10 further includes a plurality of closed microchannels 25 defined in the plate 15. The plurality of closed microchannels 25 preferably lies below the plurality of wells 20. In operation, this arrangement allows gravitational force to transfer a reagent or control media from the plurality of wells 20 into the plurality of closed microchannels 25. In various embodiments, as shown for example in FIG. 1, each microchannel of the plurality of closed microchannels 25 may comprise a first portion 26 and a second portion 27, where the first portion 26 of each closed microchannel is defined at a higher level in the plate 15 than the second portion 27 of each closed microchannel. This configuration further aids the flow of the respective reagent or control media through the closed microchannels 25. In various embodiments, the plurality of closed microchannels 25 may have a width that ranges from about 10 µm to about 1 mm, and preferably ranges from about 10 µm to about 200 µm. In other embodiments, the plurality of closed microchannels 25 may have a height that ranges from about 10 µm to about 1 mm, and preferably ranges from about 10 µm to about 200 µm.

The plate 15 further includes a sample platform 30 defining a plurality of open microchannels 35. In addition, the plurality of open microchannels 35 are preferably arranged parallel to one another in a close but spaced apart configuration. In various embodiments, the plurality of open microchannels 35 may have a width that ranges from about 10 µm to about 1 mm, and preferably ranges from about 10 µm to about 200 µm. In other embodiments, the plurality of closed microchannels 35 may have a height that ranges from about 10 µm to about 1 mm, and preferably ranges from about 10 µm to about 200 µm. The plurality of closed microchannels 25 are each in communication with one of the plurality of wells 20 and one of the plurality of open microchannels 35 of the sample platform 30. In a further embodiment, the first portion of each of the plurality of closed microchannels may be coupled to the plurality of wells and the second portion of each of the plurality of closed microchannels may be coupled to the plurality of open microchannels. As shown in FIG. 2, the sample platform 30 is preferably arranged in the middle of the plate 15 so as to be centrally located relative to each of the plurality of wells 20 and plurality of closed microchannels 25. In various other embodiments, the sample platform 30 may be located anywhere in the plate or exterior to the plate, as long as the plurality of open microchannels 35 remain in communication with the plurality of closed microchannels 25.

In various other embodiments, as shown in FIG. 1, a top surface 28 of the first portion of each closed microchannel 26 may be positioned above or even with a top surface 31 of the sample platform 30. In addition, a bottom surface 29 of the second portion of each closed microchannel 27 may be positioned even with a bottom surface 36 of the plurality of open microchannels 35. In an alternative configuration, the first portion of each closed microchannel may be arranged horizontally within the plate and the second portion of each closed microchannel may be arranged vertically within the plate. The plurality of closed microchannels 25 may have many other functional arrangements to transfer reagents and culture media to the plurality of open microchannels.

In another embodiment, the microfluidic apparatus 10 further includes a removable porous membrane 40 disposed on a top surface 31 of the sample platform 30. In operation, a tissue sample 45 is arranged on the membrane 40, and the membrane 40 is then placed on the sample platform 30. Once the tissue sample 45 has been perfused with reagents and control media, the membrane 40 and tissue sample 45 may be removed from the microfluidic apparatus 10 for analysis or further processing. In some embodiments, the membrane 40 may have vertical pores for directed flow to the tissue sample 45, which results in increased resolution of the various drug interactions with the tissue sample 45. In other embodiments, the membrane 40 may have a high porosity ranging from about 50% to about 90%, which increases tissue viability. The combination of vertically arranged pores and high porosity is particularly advantageous. In addition, the membrane 40 may comprise polyethylene terephthalate ("PET") or polytetrafluoroethylene ("PTFE"), or combinations thereof, for example.

Figure 5:
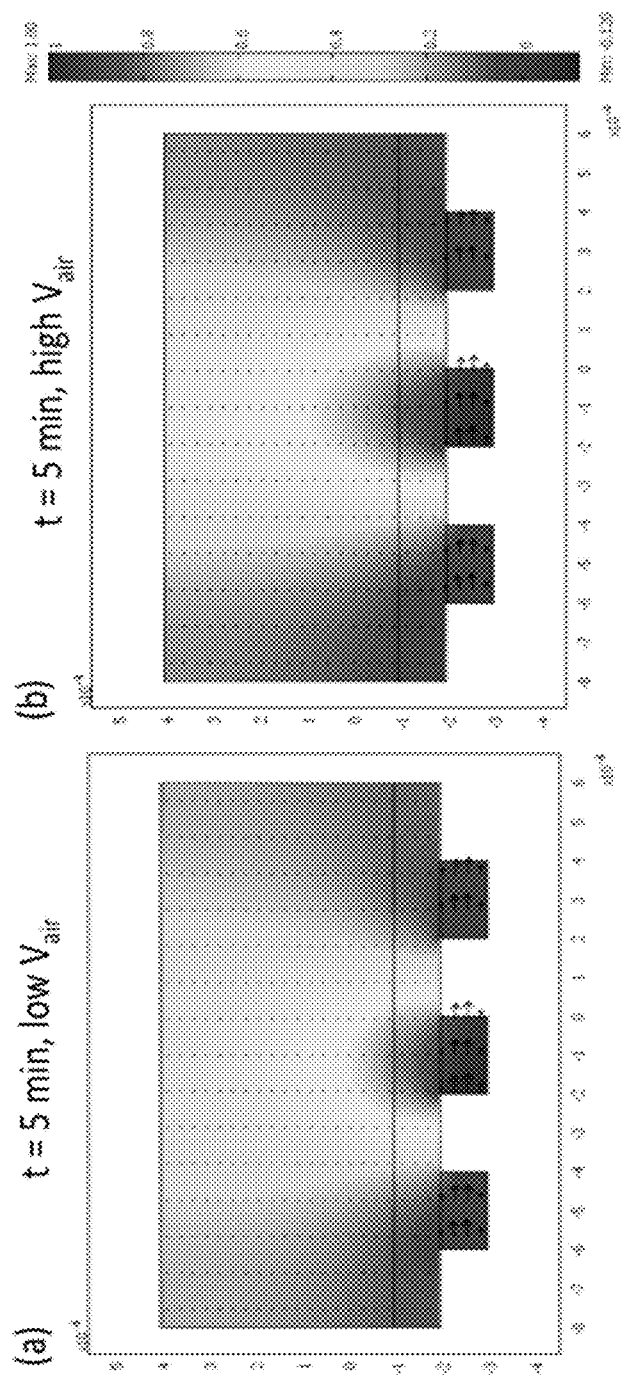
FIG. 5 is a 2D time-dependent simulation model of a cross-section of a tissue sample, a porous membrane and a plurality of open microchannels according to an example embodiment showing (a) the effect of a low air flow rate and (b) the effect of a high air flow rate.

In further embodiments, the microfluidic apparatus 10 includes an incubator (not shown) configured to receive the plate 15. The incubator maintains optimal temperature, humidity, air flow and other conditions such as carbon dioxide and oxygen content of the enclosed atmosphere. The humidity may range from about 80 to about 99 percent and preferably ranges from about 90 to about 95 percent. The temperature preferably ranges from about 35 to about 37.5° C. and may be broader in various embodiments. The elected temperature is preferably maintained at the same setting throughout the duration of the perfusion of reagents and control media. The air flow rate is typically static or the minimal air circulation present in incubators. As discussed in Example 1 below and as shown in FIGS. 5(a-b), higher air flow rates aid accelerate perfusion of the reagents and control media in to the tissue sample 45.

Figure 3:
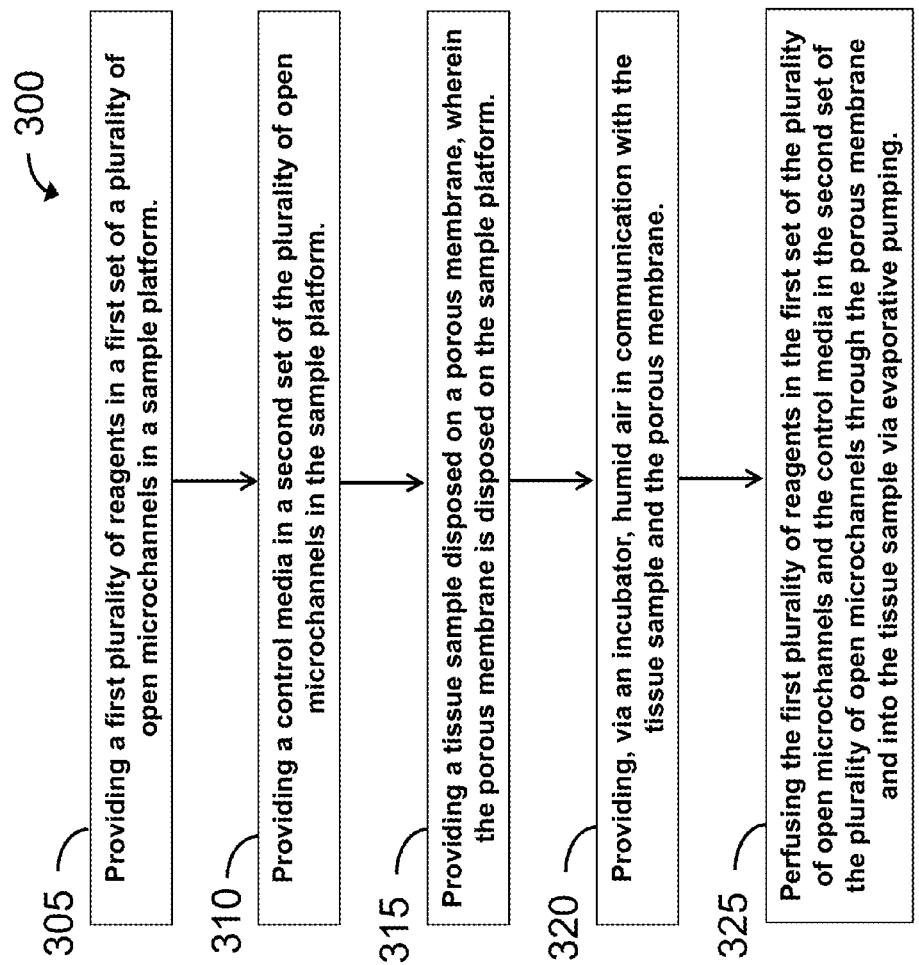
FIG. 3 is a method according to an example embodiment.

FIG. 3 is a flow chart of a method 300 that is provided that includes the step 305 of providing a first plurality of reagents in a first set 37 of a plurality of open microchannels 35 in a sample platform 30 and the step 310 of providing a control media in a second set 38 of the plurality of open microchannels 35 in the sample platform 30. The plurality of reagents and the control media may be delivered into the plurality of wells 20 of the plate 15 via a pipette 50, for example. As discussed above, in some embodiments, the reagents and control media flow into the plurality of closed and open microchannels 25, 35 via gravity. In other embodiments, a syringe pump in communication with a free end of each of the plurality of open microchannels 35 may be utilized to prefill the plurality of open and closed microchannels 25, 35 with reagents and control media. Method 300 further includes the step 315 of providing a tissue sample 45 disposed on a porous membrane 40, where the porous membrane 40 is disposed on the sample platform 30. Method 300 also includes the step 320 of providing, via an incubator, humid air in communication with the tissue sample 45 and the porous membrane 40. In addition, method 300 includes the step 325 of perfusing the first plurality of reagents in the first set 37 of the plurality of open microchannels 35 and the control media in the second set 38 of the plurality of open microchannels 35 through the porous membrane 40 and into the tissue sample 45 via evaporative pumping.

In various other embodiments, the method 300 may further include the steps of rotating the membrane 40 and perfusing a second plurality of reagents into the tissue sample 45. Rotating the membrane 40 permits additional assays to be performed for the same or different reagents on the same tissue sample 45. This rotation results in a checkerboard of reagents on the tissue sample 45, providing data for combined and single reagent effects from a second assay to evaluate combinatorial therapies, as well as single reagents. Once the assays have been completed, the tissue cores or slices may be fixed and processed for histopathologic analysis to provide data on the composition of the tissue sample and the response to individual reagent treatment streams from the first set 37 of the plurality of open microchannels 35, for example.

In preferred embodiments, the first set 37 and the second set 38 of the plurality of open microchannels 35 are arranged parallel to each other. In this arrangement, each microchannel of the second set 38 of the plurality of open microchannels 35 is arranged in between two microchannels of the first set 37 of the plurality of open microchannels 35. The effect is that a microchannel containing a control media 38 is positioned in between each microchannel containing a reagent 37. Such an arrangement helps to prevent or minimize cross-contamination or bleed-over between reagents perfused into the tissue sample 45. In further embodiments, two or more microchannels of the second set of the plurality of open microchannels may be positioned in between two microchannels of the first set of the plurality of open microchannels. This arrangement increases the control areas of the tissue sample 45 in which control media is perfused.

In various embodiments, the method 300 is performed for a period of time ranging from about twenty-four hours to about seventy-two hours. The period of time is selected to permit reagents to act over a cell cycle and during S-phase to provide a more detailed assessment of any cell death that may occur. In various embodiments, cell death may be measured by live cell imaging, for example, using fluorescent caspase activity substrates.

The method may be performed using any of the embodiments of the microfluidic apparatus 10 described above. The above detailed description describes various features and functions of the disclosed apparatus and methods with reference to the accompanying figures. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Example 1

Evaporation Model

Figure 4:
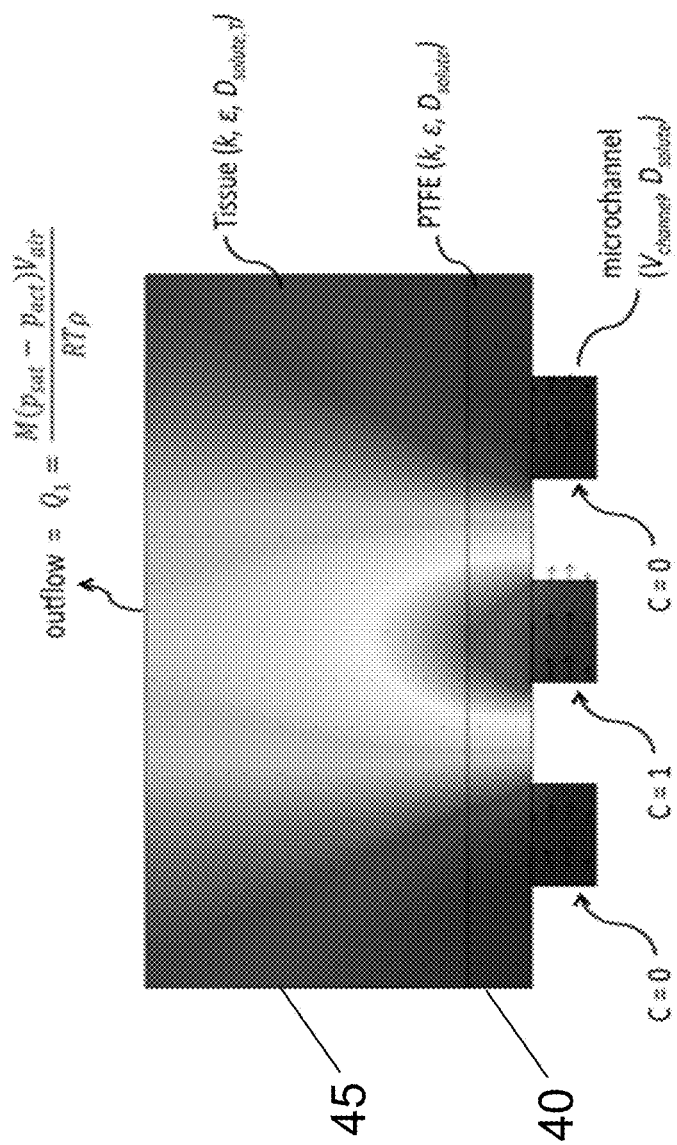
FIG. 4 is a 2D model of a cross-section of a tissue sample, a porous membrane and a plurality of open microchannels according to an example embodiment.

The microfluidic apparatus utilizes the phenomenon of evaporative pumping to control fluid transport through a tissue sample. In operation, water is lost at the air-fluid interface on the top surface of the tissue sample due to evaporation. This loss is compensated by capillary pumping of fluid from the open microchannels in the sample platform through the subdomains of a PTFE membrane and tissue sample. A small cross-section of the device is described with the 2D model shown in FIG. 4, which was generated using COMSOL Multiphysics finite-element software. As shown in FIG. 4, three open microchannels flow along the PTFE membrane subdomain for a short segment before exiting through an outlet, where the flow was induced by a syringe pump. The permeability of the PTFE is low in comparison to free fluid, so that the pressure applied by the microchannel flow does not result in significant flow within the PTFE or tissue domains. However, with the evaporation constraint at the air fluid interface, there is a combination of convection and diffusion in the PTFE membrane and tissue sample subdomains. The general equation of the 2D convection and diffusion is:

$$\frac{\partial c}{\partial t} = D\left(\frac{\partial^2 c}{\partial x^2} + \frac{\partial^2 c}{\partial y^2}\right) - C\left(\frac{\partial u}{\partial x} + \frac{\partial v}{\partial y}\right)$$

where D is the diffusion coefficient of the solute, c is the concentration of the solute, u the x-component of the fluid velocity, and v the y-component of the fluid velocity. In FIG. 4, c=1 represents a pure reagent before introduction into the microfluidic apparatus and c=0 represents pure control media before introduction into the microfluidic apparatus. In our case the flow imposed on the tissue sample and PTFE membrane subdomain is contributed primarily from the evaporative pumping. The flow imposed at the air-fluid interface from evaporation is $$Q = \frac{M(p_{sat} - p_{act})U_{air}}{RT\rho}$$

where M is the molecular weight of water [18×10-3 kg mol-1], $p_{sat}$ [Pa] the water vapor pressure at saturation for the given temperature, $p_{act}$ [Pa] the water vapor pressure of the ambient air, $U_{air}$ [m/s] the velocity of air in contact with the air-fluid interface, R the gas constant [8.314 m3 Pa K-1 mol-1], the absolute temperature T [K], and the fluid density ρ [1×103 kg m-3]. The actual vapor pressure is calculated from the relative humidity and known vapor pressures at saturation using:

$$\text{Relative humidity} = \frac{p_{act}}{p_{sat}} \times 100$$

Thus, the flow from evaporation depends primarily on the velocity of the air and the relative humidity with constant temperature. FIG. 5 shows one example of time-dependent simulations for a low (FIG. 5(a)) and high flow rate (FIG. 5(b)) of air at the interface shown. The noticeable difference in these simulations is the extent to which the air flow drags the concentration gradient through the tissue sample over time. Thus, the simulation shows that high air flow accelerates perfusion into the tissue.

Example 2

A Microfluidic Apparatus for Exposing Tumor Biopsy Tissue to Multiple Drugs

This Example demonstrates a novel and practical microfluidic approach for culturing live tumor biopsies and multiplexing their exposure to chemotherapy drugs. The microfluidic apparatus used offered 80 individually addressable streams via open microchannels that enabled stimulation of multiple areas on a biopsy tissue and allowed explant culture of a full tissue core biopsy while preserving the tumor microenvironment. Specifically, biopsy tissues from mouse livers were used to provide data including staining of distinct micro-domains on single biopsy tissues and intracellular delivery. The results demonstrated the feasibility of a novel preclinical paradigm with great potential for predicting drug responses in cancer patients.

Theory

Core biopsy tissue from a tumor is a suitable model for drug testing, because the biopsy tissue preserves the tissue architecture and is compatible with the clinical approach. To achieve this model, the core biopsy was cultured following the "organotypic culture" technique used for brain slices, whereby the tissue is placed on top of a PET porous membrane, the cell culture medium is placed below the PET membrane, and the tissue is left in contact with air to maintain viability (see FIG. 1). The tissue was hydrophilic and was in contact with humidified air, so it was permanently moist. The evaporation at the air-fluid interface plays a crucial role in nutrient transport through the tissue to maintain viability. In order to achieve user friendliness, the apparatus had a microfluidic input interface based on a 96-well plate and enables the multiplexed delivery of large numbers of reagents (see FIG. 6B(b)). The reagents were pipetted into the wells of the 96-well plate and were delivered to the tissue (see FIG. 6B(c)) through a network of microchannels that were bonded underneath the 96-well plate.

Device Fabrication and Operation

Figure 6A:
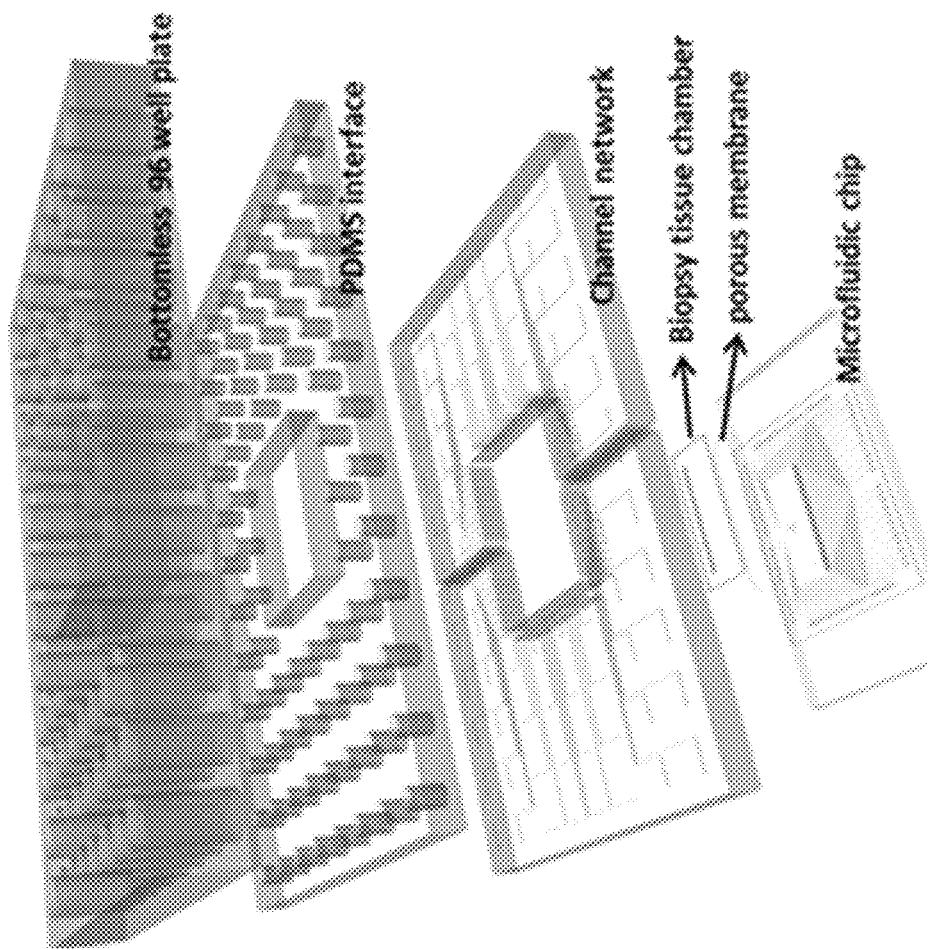
FIG. 6A is an exploded view of the microfluidic apparatus according to an example embodiment.
Figure 6B:
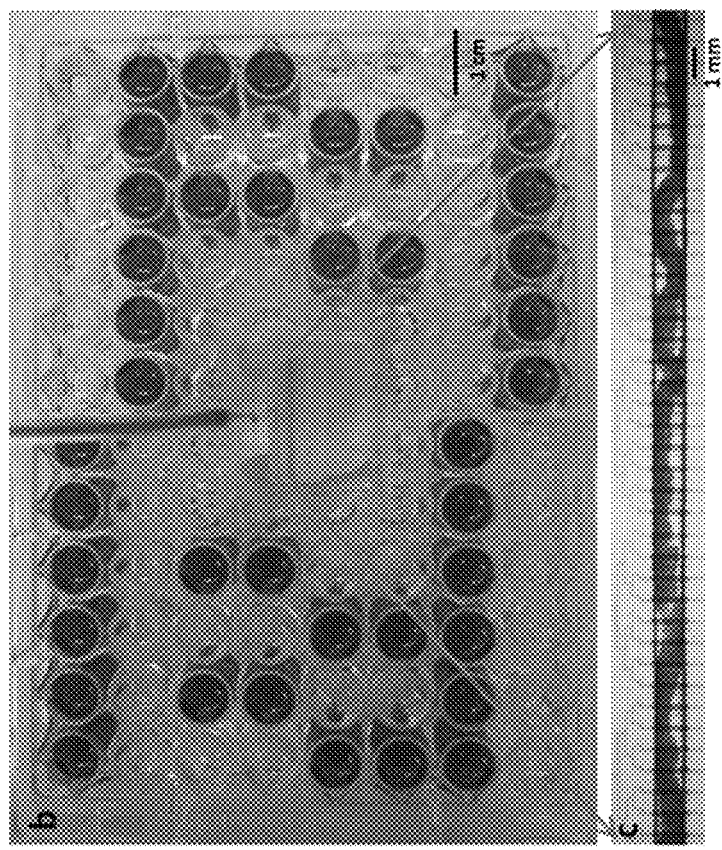
FIG. 6B shows images of two liver biopsies placed on a PET porous membrane disposed on top of a sample platform, where red colored streams are shown perfused through the bottom of the tissue sample according to an example embodiment.

The device included a 96-well plate, a poly(dimethylsiloxane) ("PDMS") interconnect layer, a microchannel network layer, and a central area defining a microfluidic chip or sample platform for receiving the tissue sample (FIG. 6A). The first layer is a bottomless 96-well plate with a modification defining a square reservoir in the center of the plate. The modification was done by cutting the plate with a rotary tool and sacrificing an area equal to 4×4=16 wells. Thus the apparatus only accepted 80 inputs into the wells, instead of 96. The second layer was a PDMS interface containing 3-mm holes and a central square. This was done by exclusion molding from a laser-cut rectangular mold to create a uniform rectangular PDMS block, followed by punching 3-mm holes and cutting the central square to match the modified 96 well plate. The third layer consisted of two separate PDMS molds to assemble a complete channel network to distribute the fluids from the well inlets to the tissue sample. This layer was fabricated using photolithography to create a SU8 master of microchannels on a silicon wafer, laser-cut acrylic sheet to attach to the wafer to define the shape of the PDMS replica, and exclusion molding to create a uniform thickness of the PDMS replica (the thickness is the same as the acrylic sheet). Then, a 0.5-mm punch was used to punch through the PDMS replica to allow the fluids to flow into the microfluidic chip or sample platform. The fourth layer is a microfluidic chip or sample platform that defined 80 individual open microchannels in parallel. These channels were disposed underneath a PET porous membrane, on top of which a biopsy tissue culture chamber sits. The microchannel network layer connected the wells with the central chip or sample platform in order to deliver the reagents. The flow rates of all channels were equilibrated by adjusting the microchannel resistances (i.e., by changing the channel widths according to the channel lengths). Bonding of PDMS to PDMS was done by oxygen plasma and PDMS to plastic was done by a surface modification using aminopropyltriethoxysilane ("APTES") coating. The central microfluidic chip or sample platform was integrated within the well plate to accommodate standard microscopy platforms. The apparatus was operated by gravity flow and the total flow rate was driven by a syringe pump through an outlet. Therefore, one tube controlled by a syringe pump was able to create 80 fluidic streams.

Mouse Liver Biopsy Extraction

Figure 6C:
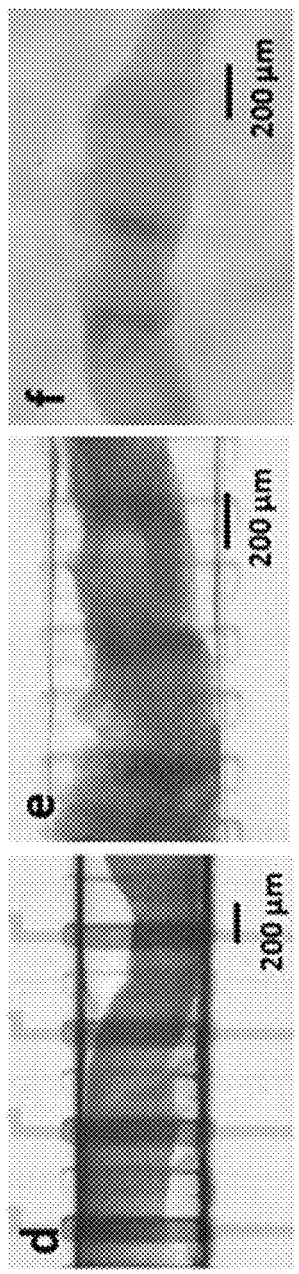
FIG. 6C shows images of red dye staining of liver biopsy tissues, specifically (d) shows the tissue sample after red colored dye perfused into the tissue from the open microchannels for two hours, (e) shows a top view of the tissue sample disposed on the microfluidic apparatus and flushed with HBSS and (f) shows a top view of the tissue sample removed from the microfluidic apparatus, illustrating selective transfer from the fluidic streams in open microchannels of the sample platform to the liver tissue.

Since the heterogeneity of tumor tissue can be a confounding factor in the analysis of results, healthy mouse liver was used as the tissue samples for the first proof-of-concept experiments. Mouse liver slice culture has been shown in many research groups as a model for toxicity testing and is able to provide homogeneous tissue biopsies to allow verification of the diffusion model of the microfluidic apparatus. To extract liver biopsies, the liver was first resected from a mouse, then was quickly transferred to ice cold Hanks' balanced salt solution ("HBSS"). A 20-gauge biopsy instrument (Angiotech, Pa.) was used to extract multiple liver biopsies with a diameter of 600 µm from one mouse liver, after which the liver biopsy tissues were transferred to the device (FIGS. 6B(b-c)) using a transfer pipette. The distinct micro-domains of red food-coloring stains on liver biopsy tissues are shown in FIGS. 6C(d-f).

Results—Intracellular Micro-Domain Delivery

Figure 7:
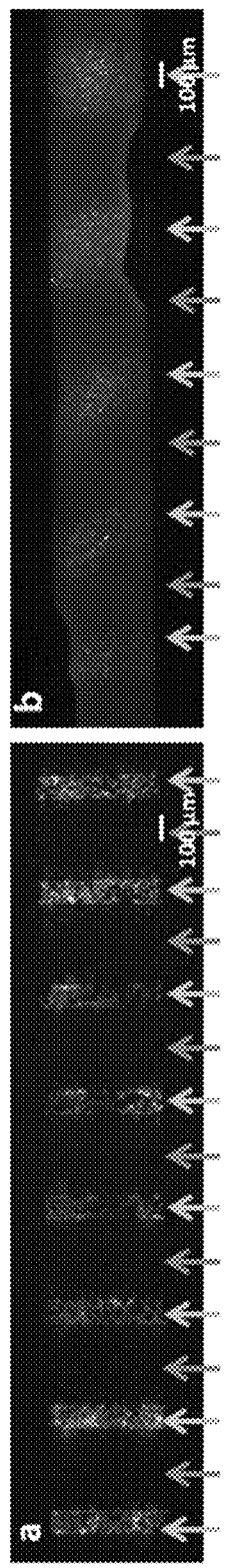
FIG. 7 shows (a) an image of a monolayer of human fibroblast cells seeded on a PET membrane selectively stained with CellTracker and (b) an image of a liver biopsy tissue that was selectively stained with CellTracker.

Green fluorescent chloromethyl derivatives of fluorescein diacetate (CMFDA, CellTracker Green) were used as a staining reagent to visualize diffusion transport to live cells. GM639 was seeded with human fibroblast cells in the microfluidic apparatus device and sat undisturbed for 3 hours to allow cells to attach to the PET membrane. Cell-Tracker solution (1 µM) and HBSS were then pipetted into the alternative channels to allow both solutions to flow beneath both the membrane and the cells for 40 minutes before the images were acquired (FIG. 7($a$)). The micro-domain staining of the monolayer of attached cells was distinguishable and allowed verification of the diffusion through the PET porous membrane from the bottom fluids to the cells. Additionally, a mouse liver biopsy tissue was used with the same experimental conditions as the dissociated cells to test the diffusion transport to the tissue. As seen in the results in FIG. 7($b$), the micro-domain staining was only observed in a 2-dimensional view but there was no cross-diffusion seen in this CellTracker experiment. The additional use of confocal microscopy will be applied to see the diffusion in a three-dimensional manner.

Conclusion

The foregoing evidences successful fabrication of a novel microfluidic apparatus that enables the culture and multiplexing of large numbers of reagents on one piece of biopsy tissue. Using a biopsy tissue allows for extracting a large amount of biological information with minimum invasiveness to the patients. Moreover, using an intact biopsy tissue preserves the tumor microenvironment, requires no additional procedures to the tissue (no additional tissue sectioning or dissociation) and matches the standard procedure of tumor diagnosis. This microfluidic device enables testing of a large amount of drugs on a tumor biopsy to predict drug responses in cancer patients and is able to provide fast and accurate results. The apparatus also has a user-friendly interface which is operated by pipetting. The preliminary results demonstrated the feasibility of a new paradigm for predicting personalized chemotoxicity response profiles based on intact biopsy tissues.

Example 3

A 96-Well, Plate-Based Microfluidic Apparatus for Multiplexed Chemosensitivity Testing on Intact Tissues Introduction The ability to predict a patient's response to chemotherapy before drugs are administered is a major challenge in oncology. Current drug testing assays are either based on cell lines, which enable high-throughput screening but lack the physiological relevance of the tumor microenvironment, or on xenograft models, which are time- and resource-intensive and may lack important tumor components such as host-derived microvasculature, immune and stromal cells. As a result, drug candidates that emerge from drug screens often prove to be ineffective when they are finally tested in humans. The following demonstrates the potential of using an intact tissue slice in conjunction with an integrative microfluidic apparatus as model for drug testing. Using intact tissues preserves the tumor microenvironment of the primary cancer tumor and provides the ability to quickly obtain chemosensitivity response results. The microfluidic apparatus enables intact tissue culture and allows for large-scale drug screening of an intact tissue slice. This approach holds a great potential for the quick and effective determination of responsiveness to anticancer drugs.

Theory

Figure 8:
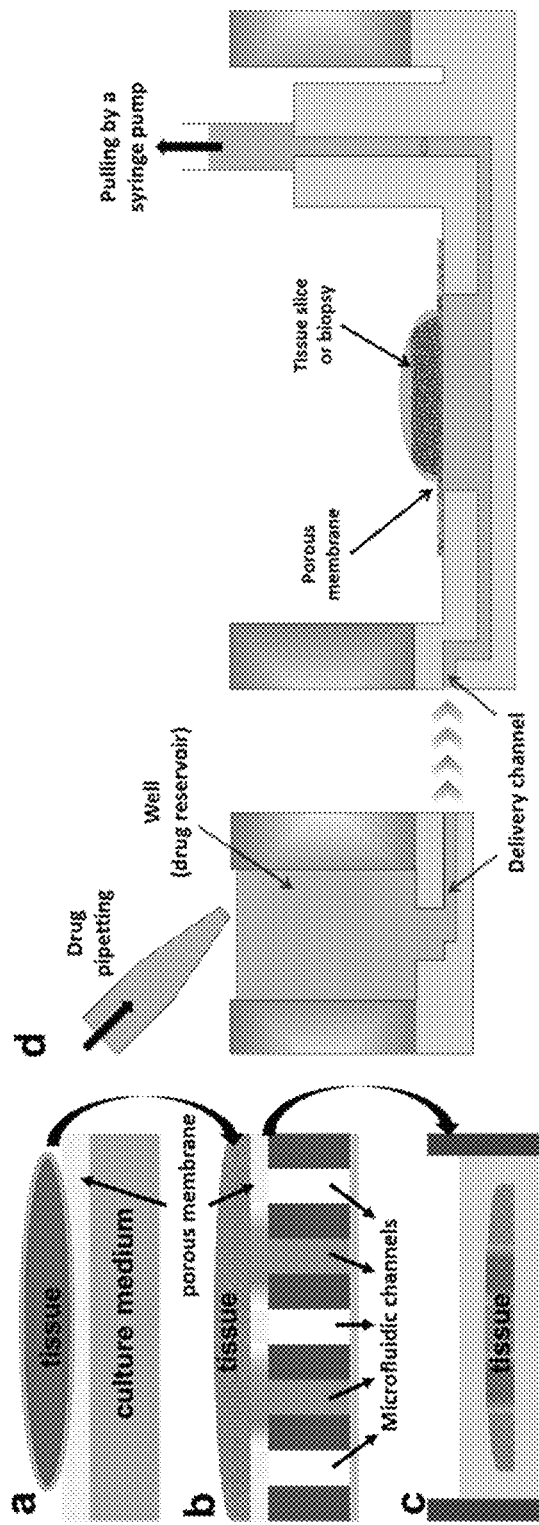
FIG. 8 shows (a) the initial tissue slice culture with the tissue sample disposed on a PTFE membrane, (b) the tissue sample and membrane disposed on a sample platform of a microfluidic apparatus, (c) the tissue sample in a post-reagent exposure bath for tissue processing and (d) a cross-sectional view of the microfluidic apparatus according to an example embodiment.

The tissue slice was cultured following the "organotypic culture" technique used for brain slices, whereby the tissue is placed on top of a hydrophilic polytetrafluoroethylene ("PTFE") porous membrane, the cell culture medium is placed below the PTFE membrane, and the tissue is left in contact with air to maintain viability. The tissue is hydrophilic and is in contact with humidified air to create an air-fluid interface that allows oxygen and nutrient transport through the tissue slice. In the organotypic tissue slice culture, a membrane-transfer technique was devised that allows for transfer of the tissue slice from the initial tissue slice culture (FIG. 8$a$), to the sample platform of the microfluidic apparatus (FIG. 8$b$) and also to the post-exposure bath tissue processing (such as immunocytochemistry or tissue clearing) (FIG. 8$c$). Hydrophilic PTFE membranes form a tight seal on poly(dimethylsiloxane) ("PDMS"), acting as a roof atop a plurality of open microchannels (FIG. 8$b$). Therefore, flow streams can be generated in the microchannels and transported to the membrane in a spatially-defined formation. A 96-well, plate-based microfluidic apparatus was developed to accommodate the membrane-transfer technique and to allow a large amount of reagents to be delivered to an intact tissue slice (FIG. 8$d$). The device has a microfluidic input interface based on a 96-well plate and enables the multiplexed delivery of a large number of reagents. The reagents can be pipetted into the wells of the 96-well plate and are delivered to the tissue through a network of microchannels that are bonded underneath the 96-well plate. This approach affords large-scale drug screening in organotypic tissue slice culture and allows for post-tissue processing by using conventional pathological techniques (i.e., the tissue slice can be detached from the device for further analysis).

EXPERIMENTAL

Overview of the Device

Figure 9:
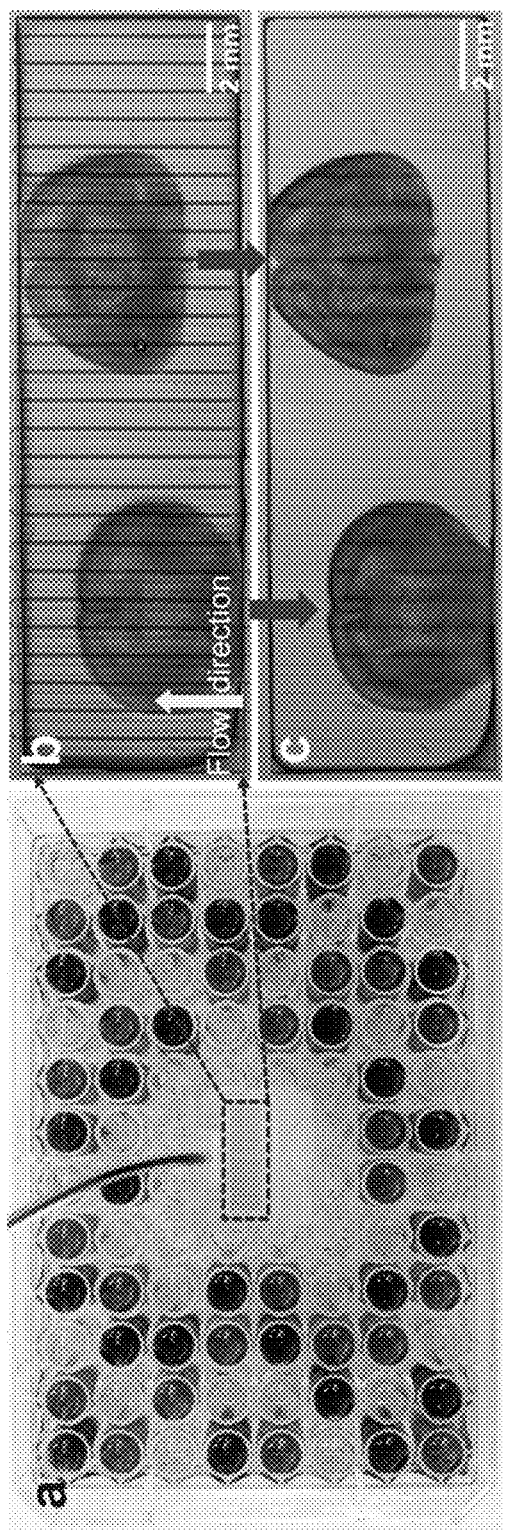
FIG. 9 shows (a) a microfluidic apparatus, according to an example embodiment, having 80 wells, (b) a top view of a tissue sample on a membrane disposed on a sample platform of the microfluidic device and the delivery streams in a plurality of open microchannels and (c) a top view of the tissue sample showing reagents patterned on the tissue sample after perfusion of reagents into the tissue.

The device includes a bottomless 96-well plate, a poly (dimethylsiloxane) ("PDMS") interconnect layer, a microchannel network layer, and the central area of the microfluidic chip (where the tissue is placed). All the components are bonded irreversibly by using oxygen plasma for PDMS to PDMS and aminopropyltriethoxysilane ("APTES") for PDMS to thermoplastics, as a leak-proof device. The device is designed to allow all reagents to be loaded by pipetting, and the flow rate of all delivery streams in the plurality of open microchannels is controlled by an outlet (FIG. 9$a$). The tissue slice is initially cultured on a hydrophilic PTFE porous membrane well insert (Millipore, Mass.), then can be transferred to the device by cutting the PTFE membrane out from the well insert and then placing it onto the sample platform above the open microchannels of the microfluidic apparatus. The microfluidic apparatus was tested with food coloring dyes to visualize all the channels and the fluidic streams. Two 300-µm thick fixed mouse brain slices were then placed on top of the porous membrane to test the fluid transport. The streams can be formed without concerns about bubble formation, and the fluidic streams quickly flow through the porous membrane, leaving the food coloring dye on the mouse brain slices (FIG. 9b). Even after the delivery channels were rinsed with clear phosphate buffered saline ("PBS"), the colored stains were still visible on the slices (FIG. 9c).

Drug Testing on Human GBM Xenograft Slices

Two hundred thousand (200,000) viable glioma cells labelled by lentiviral GFP expression were orthotopically injected in the brain of an immunodeficient mouse following proper protocols. After approximately four weeks of tumor growth, the mouse was sacrificed and the mouse brain was then transported in ice cold culture medium prior to slicing. A vibratome tissue slicer was used to produce 400 µm-thick slices from a GBM xenograft mouse brain (the tissue was submerged in oxygenated ACSF during the slicing process). Then the slices were quickly transferred onto the PTFE membrane well inserts with pre-warmed culture medium and placed in an incubator. These slices were cultured for at least 24 hours (recovery) before being used for drug testing.

To proceed with drug testing, the GBM slice was transferred from the culture membrane well insert to the microfluidic apparatus by cutting the PTFE membrane out from the well insert and then placing it onto the plurality of open microchannels of the apparatus. Once the slice was on the device, we imaged the full culture area of the device to determine the position of the slice. Then the wells corresponding to the determined drug delivery channels were replaced with drug solution (1 mM of TMZ in culture medium; TMZ was chosen due to its clinical relevance to GBM), and then the apparatus was connected to a syringe pump with the total flow rate of 300 µL per hour in an incubator to initiate the drug delivery. The GBM slice was exposed selectively to TMZ (the slice regions without TMZ exposure were exposed to normal culture medium as control) for 48 hours before imaging.

Following drug delivery, the slice was then transferred to a glass-coverslip bottom petri dish for rinsing in PBS and imaging. GFP-labelled glioma cells were used for the dead-cell imaging readouts, which were acquired by an epifluorescence microscope and verified by confocal microscopy.

Results and Discussion

Figure 10:
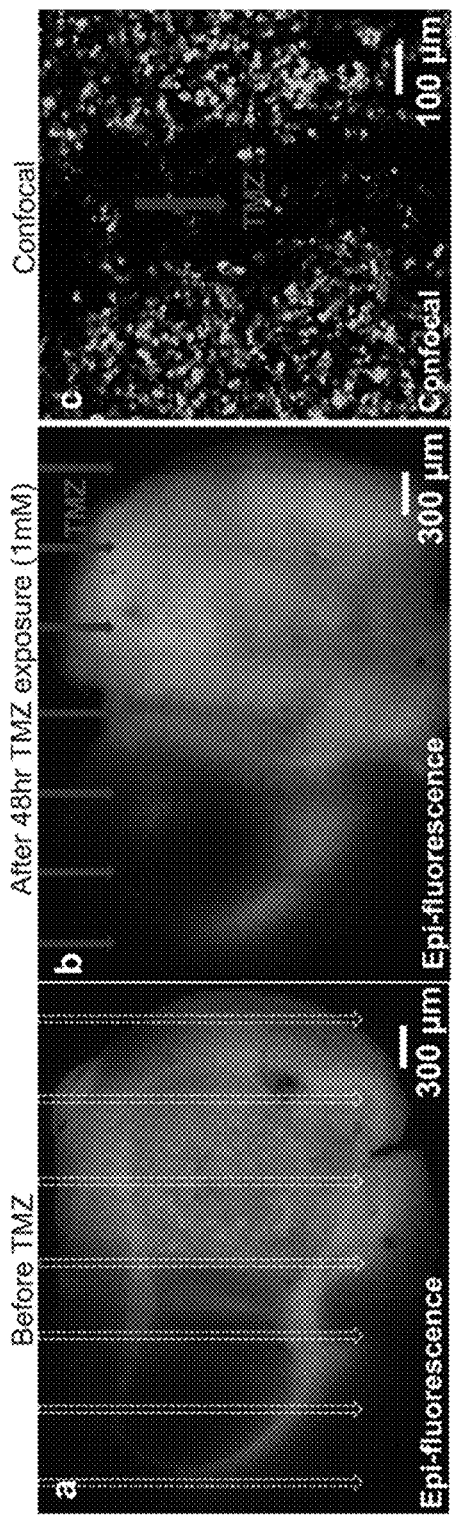
FIG. 10 shows (a) a GBM xenograft slice with GFP-labeled glioma cells prior to being treated with TMZ in the regions indicated in dashed lines, (b) the GBM xenograft slice of FIG. 10(a) after 48 hours of exposure to TMZ and demonstrating the selectivity of cell death in the TMZ region and (c) a confocal image of a defined track of GFP-labeled GBM cell loss along one of the TMZ flow tracks shown in FIGS. 10(a) and (b).

Our results demonstrate that defined fluidic streams can be delivered through a porous membrane to intact tissue slices in a spatially-defined manner (FIGS. 9b-c). In the TMZ drug delivery experiment, a human GBM mouse xenograft slice was selectively exposed to TMZ for 48 hours following by imaging. In the epifluorescence images, the loss of GFP-labelled glioma cells (loss of GFP expression indicates the cell death) formed tracks at the TMZ exposure regions (FIGS. 10a-b). The tracks at the TMZ exposure regions are faint, because the drug did not fully penetrate the full thickness of the slice. Thereby, the epifluorescence image only shows the shadows of tracks from the whole optical volume of the slice. In further examination by using a confocal microscope, the tracks of dead cells can be easily found with clear contrast.

The foregoing demonstrates the preliminary use of GFP-labeled cells to identify the selective cell death in a GBM xenograft slice at TMZ-exposed regions. In this approach, the tissue slice can be transferred to a separate dish or container after drug screening for further immunohistological process. Thereby, the tissue slice can be labeled with multiple biomarkers to identify crucial mechanisms of cellular responses by conventional histopathological methods. Furthermore, readouts from confocal microscope or thin tissue sectioning can be quantified and be used to guide the selection of a drug with potential effectiveness.

CONCLUSION

A novel microfluidic apparatus was fabricated to support human tumor organotypic slice cultures that can be used to perform the multiplexed screening of up to as many as eighty different drugs or drug combinations on single tumor tissue slices. This apparatus is being used to perform drug response screening of primary human tumors to identify potentially useful drugs or drug combinations for individual tumors and patients and minimize avoidable toxicity. The preliminary results demonstrate the feasibility of this approach to predict drug responses in cancer patients based on intact tumor tissue slices.

The invention claimed is:

1. A microfluidic apparatus, comprising:
   a plate;
   a plurality of wells defined in the plate;
   a plurality of closed microchannels defined in the plate, wherein each closed microchannel of the plurality of closed microchannels comprises a first portion and a second portion, wherein the first portion of each closed microchannel is defined at a higher level in the plate than the second portion of each closed microchannel; and
   a sample platform defining a plurality of open microchannels, wherein the plurality of closed microchannels are each in communication with one of the plurality of wells and one of the plurality of open microchannels of the sample platform.

2. The microfluidic apparatus of claim 1, wherein a top surface of the first portion of each closed microchannel is positioned above or even with a top surface of the sample platform.

3. The microfluidic apparatus of claim 1, wherein a bottom surface of the second portion of each closed microchannel is positioned even with a bottom surface of the plurality of open microchannels.

4. The microfluidic apparatus of claim 1, wherein the first portion of each closed microchannel is coupled to the plurality of wells and the second portion of each closed microchannel is coupled to the plurality of open microchannels.

5. The microfluidic apparatus of claim 1, wherein the first portion of each closed microchannel is arranged horizontally within the plate and the second portion of each closed microchannel is arranged vertically within the plate.

6. The microfluidic apparatus of claim 1, wherein the plurality of open microchannels have a width that ranges from about 10 µm to about 1 mm.

7. The microfluidic apparatus claim 1, wherein the plurality of open microchannels have a height that ranges from about 10 µm to about 1 mm.

8. The microfluidic apparatus of claim 1, wherein the plurality of wells comprises 10 to 100 wells.

9. The microfluidic apparatus of claim 1, wherein the plurality of open microchannels are arranged parallel to one another in a close but spaced apart configuration.

10. A microfluidic apparatus, comprising:
a plate;
a plurality of wells defined in the plate;
a plurality of closed microchannels defined in the plate;
a sample platform defining a plurality of open microchannels, wherein the plurality of closed microchannels are each in communication with one of the plurality of wells and one of the plurality of open microchannels of the sample platform; and
a removable porous membrane disposed on a top surface of the sample platform.

11. The microfluidic apparatus of claim 10, wherein the membrane comprises vertical pores.

12. The microfluidic apparatus of claim 10, wherein the membrane has a high porosity ranging from about 50% to about 90%.

13. The microfluidic apparatus of claim 10, wherein the membrane comprises polyethylene terephthalate or polytetrafluoroethylene, or combinations thereof.

14. The microfluidic apparatus of claim 1, further comprising an incubator configured to receive the plate.

15. A method for use of the microfluidic apparatus of claim 1, the method comprising:
providing a first plurality of reagents in a first set of the plurality of open microchannels in the sample platform;
providing a control media in a second set of the plurality of open microchannels in the sample platform;
providing a tissue sample disposed on a porous membrane, wherein the porous membrane is disposed on the sample platform;
providing, via an incubator, humid air in communication with the tissue sample and the porous membrane; and
perfusing the first plurality of reagents in the first set of the plurality of open microchannels and the control media in the second set of the plurality of open microchannels through the porous membrane and into the tissue sample via evaporative pumping.

16. The method of claim 15, further comprising rotating the membrane on the sample platform and perfusing a second plurality of reagents into the tissue sample.

17. The method of claim 15, wherein the first set and the second set of the plurality of open microchannels are arranged parallel to each other, wherein each microchannel of the second set of the plurality of open microchannels is arranged in between two microchannels of the first set of the plurality of open microchannels.

18. The method of claim 15, wherein the method is performed for a period of time ranging from about twenty-four hours to about seventy-two hours.

* * * * *